United States Patent [19]

Kuraoka et al.

[11] Patent Number: 4,462,215
[45] Date of Patent: Jul. 31, 1984

[54] METHOD OF PRESERVING ORGAN AND APPARATUS FOR PRESERVING THE SAME

[75] Inventors: Yasuo Kuraoka; Nobuo Sakao, both of Sapporo, Japan

[73] Assignee: Hoxan Corporation, Sapporo, Japan

[21] Appl. No.: 499,220

[22] Filed: May 31, 1983

[51] Int. Cl.³ .............................................. F24F 3/16
[52] U.S. Cl. ........................................ 62/78; 62/306; 62/514 R; 165/2; 435/1
[58] Field of Search ...................... 62/78, 306, 514 R; 435/1; 165/14, 2

[56] References Cited

U.S. PATENT DOCUMENTS

| | | | |
|---|---|---|---|
| 3,406,531 | 10/1968 | Swenson et al. | 62/78 |
| 3,545,221 | 12/1970 | Swenson et al. | 62/78 |
| 3,545,225 | 12/1970 | Swenson et al. | 62/78 |
| 3,607,646 | 9/1971 | Roissart | 435/1 |
| 3,881,990 | 5/1975 | Burton et al. | 435/1 |
| 3,892,628 | 7/1975 | Thorne et al. | 435/1 |
| 3,914,954 | 10/1975 | Doerig | 62/306 |
| 4,008,754 | 2/1977 | Kraushaar et al. | 62/78 |
| 4,186,565 | 2/1980 | Toledo-Pereyra | 62/306 |
| 4,242,883 | 1/1981 | Toledo-Pereyra | 62/78 |

Primary Examiner—Ronald C. Capossela
Attorney, Agent, or Firm—George B. Oujevolk

[57] ABSTRACT

A method of preserving an organ which comprises first perfusing step of injecting blood uniformly perfusing choline from an artery or portal vein of the excised organ while gradually lowering its temperature and exhausting it from the vein continuing until the liquid is lowered to the first proximity lowering temperature before its solidifying temperature, second perfusing step of perfusing refrigerating defect preventing dimethyl sulfoxide or glycerin instead of the blood uniformly perfusing liquid while gradually lowering its temperature from the first proximity lowering temperature continuing until the agent becomes the second proximity lowering temperature before its solidifying temperature, third perfusing step of perfusing the final perfusing liquid of low solidifying temperature lower than alcohol or ether instead of the agent while gradually lowering the liquid from the second proximity lowering temperature continuing until the liquid becomes the third proximity lowering temperature before its solidifying temperature, or until the liquid is frozen.

2 Claims, 2 Drawing Figures

METHOD OF PRESERVING ORGAN AND APPARATUS FOR PRESERVING THE SAME

BACKGROUND OF THE INVENTION

This invention relates to a method of preserving an organ of various type excised from a human body for a long period or term to preserve the organ and to transplant the organ at an adequate time to an apparatus for preserving the organ to be used to perform the method.

The preservation of an excised organ to the time of transplanting the organ has heretofore been executed. The preserving apparatus is known which injecting choline at approx. 4° C. having properties similar to blood from an artery or portal vein of an organ and exhausting the blood from a vein, so-called a perfusion method. The organ which is thus treated by this perfusion method is preserved under the temperature condition of approx. 40° C. and is used after blood is applied to the preserved organ in case of the transplantation.

According to this preserving method, the organ can be preserved only for approx. 12 hours. Accordingly, the timing adjustment between the supply and the demand of the organ becomes difficult, causing large problem to save the human life.

It is considered to freeze the organ at a low temperature as the preserving temperature condition so as to prolong the preserving period of time, but when the organ is frozen according to the conventional method, a cell necrocytosis occurs, causing the organ itself to occur a meronecrosis.

SUMMARY OF THE INVENTION

Accordingly, a primary object of this invention is to provide a method of preserving an organ which can freeze the organ without occurring a cell necrocytosis and can semipermanently preserve the cell as well as which can thaw the frozen organ in case of transplanting the organ.

Another object of this invention is to provide an apparatus for preserving and thawing the frozen organ.

The above and other relates objects and features of the invention will be apparent from a reading of the following description of the disclosure found in the accompanying drawings and the novelty thereof pointed out in the appended claims.

DESCRIPTION OF THE PREFERRED EMBODIMENTS

An apparatus for preserving an organ according to the present invention will be described with respect to the embodiment disclosed in the accompanying drawings.

Figure 1:
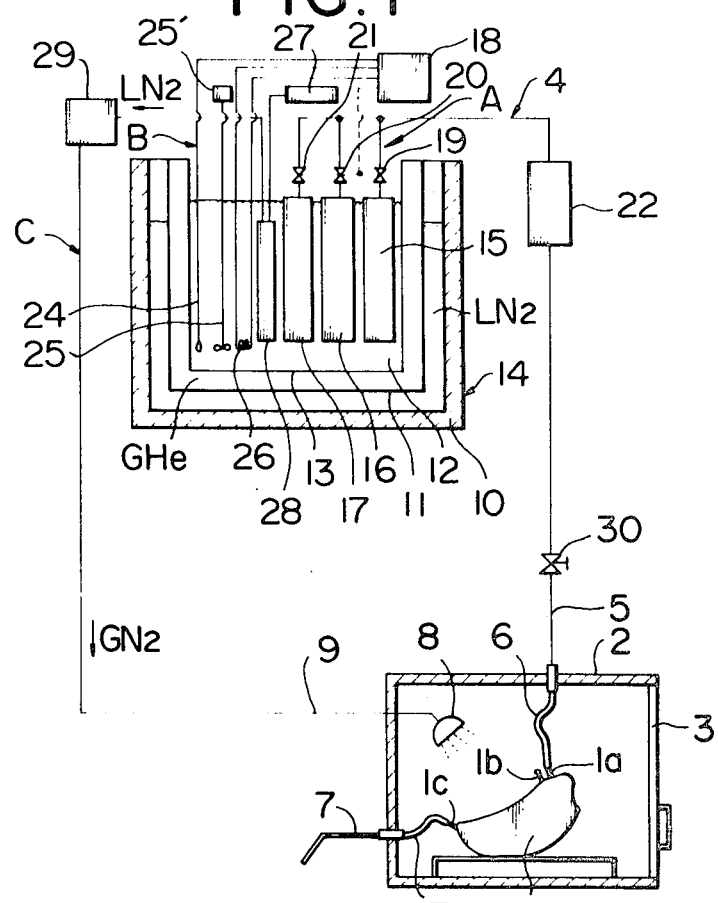
FIG. 1 is a partial longitudinal sectional view of one preferred embodiment of an apparatus for preserving an organ to executing a method of preserving the organ according to the present invention for the explanatory purpose.

In FIG. 1, a heat insulatng container 2 which can contain an organ 1 has an openable door 3. The container 2 and a perfusion freezing and thawing unit 4 are connected to a fluid supply pipe 5 of the unit 4. An inflow pipe 6 which is passed through the container 2 is connected to one end of the pipe 5. This pipe 6 is connected to the artery 1a or a portal vein 1b of the organ 1. Further, an exhaust pipe 7 which is passed through the container 2 is connected to a vein 1c. Then, a gas supply pipe 9 of the unit 4 is connected to a gas supply nozzle 8 which is provided in the container 2. The unit 4 shown in FIG. 1 stores liquefied nitrogen $LN_2$ between outer and middle tanks 10 and 11 which are thermally insulated, and a cooling tank 14 sealed with helium gas GHe between the tank 11 and an inner tank 13 which contains refrigerant 12 such as Freon. A liquid supplying mechanism A is provided in the tank 14.

In the mechanism A shown in FIG. 1, first, second and third containers, 15, 16, 17 which respectively contain choline or dimethyl sulfoxide (DMSO), glycerin and alcohol are dipped in the refrigerant 12. First, second and third control valves 19, 20 and 21 respectively provided at outflow pipes of the containers 15, 16 and 17 are suitably opened or closed under the control of a controller 18, and the choline, DMSO and alcohol are selectively supplied to the artery 1a or portal vein 1b of the organ 1 by the operation of a pump 22 provided at the pipe 5.

Figure 2:
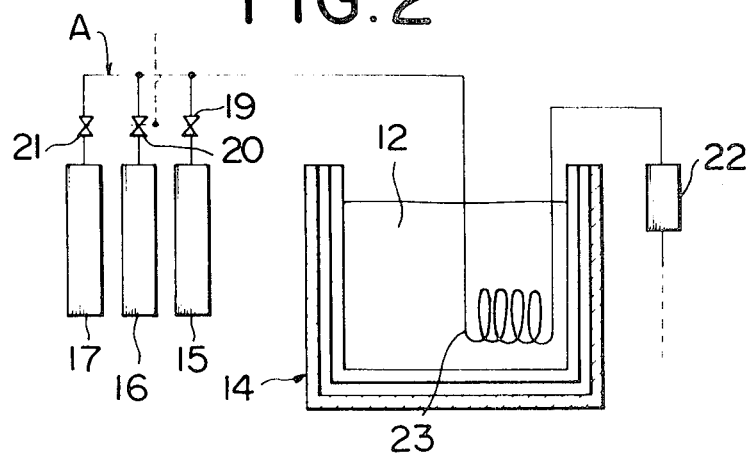
FIG. 2 is a schematic view of the essential part of another preferred embodiment of the apparatus according to the present invention for the explanatory purpose.

On the other hand, in a liquid supplying mechanism A which is schematically shown in FIG. 2, first, second and third containers 15, 16 and 17 are provided externally of the cooling tank 14, and a heat exchanger 23 formed between the first, second and third control valves 19, 20 and 21 and the pump 22 is dipped in the refrigerant 12 of the cooling tank 14.

In the tank 14 is provided a refrigerant temperature controlling mechanism B which can control the temperature of the refrigerant 12. In the embodiment exemplified in FIG. 1, a temperature sensor 24, an agitator 25 and an electric heater 26 are dipped in the refrigerant 12 in the mechanism B. The sensor 24 and the heater 26 are connected to the controller 18. Reference numeral 25' designates a motor for driving the agitator 25.

Further, in the tank 14 is provided an organ temperature controlling mechanism C. The $LN_2$ is supplied from an organ refrigerant bomb 27 which contains liquid nitrogen to a gas supplying container 28 which is disposed in the refrigerant 12, and the $LN_2$ which is supplied to the nozzle 8 through the pipe 9 as nitrogen gas $GN_2$ controlled to a predetermined temperature by a heat exchanger 29. Reference numeral 30 designates a control valve provided in the pipe 5.

In order to perform a method of preserving an organ according to the present invention with the apparatus thus constructed as described above, the first valve 19 is first opened by the controller 18, and blood uniformly perfused liquid such as choline is supplied from the container 15 by the operation of the pump 22. Thus, the liquid is flowed from the artery 1a or portal vein 1b of the organ 1 into the organ 1, and is exhausted externally from vein 1c. In this case, the liquid is injected while gradually lowering its temperature by controlling the temperature of the refrigerant 12 under the control of the mechanism B by the controller 18.

More particularly, since the excised organ 1 is initially substantially at 37° C. of human body temperature, the liquid is gradually lowered at its temperature from the body temperature. Then, the blood of the organ 1 is exhausted by the injection of the liquid into the organ 1 and is thus substituted for the liquid. Such a perfusing step is continued until the liquid becomes the first proximity lowering temperature before the solidifying temperature.

The above lowering temperature is controlled by controlling as described above the refrigerant 12 cooled through the GHe in the tank 11 from the $LN_2$ in the tank 10 by the mechanism B. Since the solidifying temperature of the choline is approx. 0° C., the first perfusing step may control the lowering temperature so that the first proximity lowering temperature becomes approx. 1° to 2° C. In order to lower, for example, the blood uniform perfusing liquid from the body temperature 37° C. to 2° C., the temperature lowering speed is 3.5° C./min, and the perfusing time can be set to approx. 10 min.

The $GN_2$ controlled at its temperature is injected from the nozzle 8 by operating the heat exchanger 29, thereby rapidly equalizing the atmospheric temperature in the container 2 to the temperature of the blood uniformly perfusing liquid to be lowered at its temperature to eliminate the temperature gradient between the inner and the outer temperatures of the organ 1. This is also continued in the following steps.

Then, the method is transferred to the second perfusing step of supplying and perfusing a freezing defect preventing agent such as dimethyl sulfoxide or glycerin in the container 16 to the organ 1 instead of the blood uniformly perfusing liquid by controlling to close the valve 19 and to open the valve 20 instead of the blood uniformly perfusing liquid.

In this step, the agent becomes the first proximity lowering temperature (2° C.). The agent is gradually lowered by controlling it with the mechanism B, and this step is continued until the agent becomes the second proximity lowering temperature before its solidifying temperature.

Since the solidifying temperature of the DMSO is approx. −5° C., the second proximity lowering temperature is preferably approx. −4° C. In fact, it takes approx. 20 min of perfusing period of time at 0.3° C./min to lower the temperature from 2° C. of the first proximity perfusing temperature to −4° C., the moisture content can be sufficiently absorbed by the agent due to the osmotic pressure difference between the agent and the moisture content in the cells of the organ 1 with the perfusion of the agent.

When the second perfusing step is thus completed, the step is then transferred tto the third perfusing step. To transfer to the third step, the valve 20 is closed, the valve 21 is opened to substitute the agent for the final perfusing liquid having a solidifying temperature lower than the above refrigerating defect preventing agent such as alcohol and to supply and perfuse the final perfusing liquid. In this step, the liquid is gradually lowering from the second proximity lowering temperature (−4° C.), is continued until the final perfusing liquid becomes the third proximity temperature before its solidifying temperature or until the perfusing liquid is frozen to stop perfusing. In case of the alcohol, since the solidifying temperature is approx. −80° C., the third proximity lowering temperature may, for example, be set to −60° C. or −80° C.

In fact, in this third step, it takes approx. 30 min of perfusing period of time at the lowering speed of 0.1° C./min. to lower the alcohol from −4° C. to −37° C., and it further takes approx. 5 min of perfusing period of time at the lowering temperature of 5° C./min. under the lowering condition from −37° C. to −60° C.

The frozen organ obtained through the first to third steps as described above is then preserved in the frozen state. In case of the above embodiment, the frozen organ may be preserved in a refrigerator which is maintained at approx. −80° C. or may be preserved in liquefied gas such as liquefied nitrogen.

The frozen organ thus preserved is then thawed for transplanting it. The thawing means can be performed substantially reversely by the steps of freezing the organ.

More particularly, the frozen organ is removed from the preserved position, and is set to the state shown in FIG. 1. In this case, the atmospheric temperature in the container 2 is first gradually lowered at its temperature, thereby raising the final perfusing liquid such as alcohol existing in a blood vessel of the organ higher than the solidifying temperature to thaw the liquid and then opening the valve 21, thereby perfusing the alcohol by the pump 22.

In the first thawing and perfusing step, the liquid is gradually raised at its temperature by the mechanism B and is continued until the liquid temperature becomes the second proximity lowering temperature (−4° C.).

Then, the method is transferred to the second thawing and perfusing step of perfusing the refrigerating defect preventing agent instead of the final perfusing liquid. In this step, the liquid is gradually raised at its temperature from the second proximity lowering temperature (−4° C.), and is continued until the temperature of the agent becomes the first proximity lowering temperature (1° to 2° C.).

Further, the blood uniformly perfusing liquid such as the choline is gradually raised at its temperature from the first proximity lowering temperature instead of the above agent and is perfused. In this third step, it is continued until the liquid becomes approx. body temperature. Thus, the organ passed through all the thawing and perfusing steps can be used for a transplantation by applying the predetermined blood to the organ.

According to the first method of the present invention as described above, the choline is not merely perfused in the organ instead of the blood as the conventional method and the organ is preserved at approx. 4° C., but the blood uniformly perfusing liquid such as choline is gradually lowered at its temperature in the first perfusing step until the liquid is perfused to the first proximity lowering temperature before its solidifying temperature. Accordingly, the organ is not affected by the influence of the abrupt temperature change, but the nutriments equivalent to the blood are supplied to the organ when the metabolism of the cells of the organ is most active at 1° to 2° C.

In the second thawing step, the refrigerating defect preventing agent is further lowered at its temperature and is lowered to the second proximity lowering temperature before the solidifying temperature of the agent. Accordingly, the moisture content in the cells is absorbed due to the osmotic pressure difference from the moisture content in the cells or the organ and the agent in this step as described above. Consequently, when the organ is frozen by the temperature fall in the next step, no moisture is contained, and the organ can be frozen without causing cell necrocytosis.

In the final third thawing step, the thawing is performed while lowering the temperature from −4° C. to −80° C. with the final perfusing liquid of low solidifying temperature lower than the agent as the perfusing liquid. Accordingly, the organ can be lowered at its temperature to considerably low state without affecting the influence of the abrupt temperature fall in the respective steps.

Therefore, according to the first embodiment of the present invention as described above, the organ can be semipermanently preserved without cell meronecrosis by preserving the frozen organ in the frozen state.

In the second embodiment of the present invention, the frozen organ preserved according to the first embodiment of the present invention provides to preserve the organ to the state capable of transplanting the organ. In this embodiment, the steps of the first embodiment is performed in concept reversely. Thus, the frozen and preserved organ as described above is gradually raised at its temperature to thaw the final thawing liquid in the blood vessel in the organ, the liquid is then gradually raised at its temperature, the first thawing and perfusing step for perfusing the liquid from the artery or portal vein to the vein until becoming the second proximity lowering temperature, the refrigerant defect preventing agent is gradually raised from the above second proximity lowering temperature instead of the final perfusing liquid, and is continued until becoming the first proximity lowering temperature, and further the blood uniformly perfusing liquid is gradually raised at its temperature from the first proximity lowering temperature instead of the agent, and is continued until becoming the body temperature in the third thawing and perfusing step of perfusing the liquid, and the predetermined blood is applied to the organ. Therefore, the frozen organ can be readily thawed without any damage.

Further, in the third embodiment of the present invention, the apparatus for preserving the frozen organ, which comprises the perfusing and thawing unit 4, and the heat insulating container 2 capable of containing the organ 1, the unit 4 having a refrigerant tank 14 containing the refrigerant 12 such as Freon and thermally insulated, the refrigerant temperature controlling mechanism B capable of controlling the temperature of the refrigerant 12 by the controller 12, the gas supplying container 28 supplied with the refrigerant from the organ refrigerant bomb 27 dipped in the refrigerant 12 for the tank 14, the container 28 having the organ temperature controlling mechanism C connected through the heat exchanger 21 to the gas supply pipe, and the liquid supplying mechanism A for selectively flowing out the liquid to be flowed out from the first container 15 for blood uniformly perfusing liquid such as choline, the second container 16 for the refrigerating defect preventing agent such as dimethyle sulfoxide or glycerin, the third container 17 for low solidifying point final perfusing liquid such as alcohol under the control of the controller 18 to the liquid supply pipe 5, the mechanism C being connected via the pipe 9 to the nozzle 8 in the container 2, and the mechanism A being connected to the artery 1a or portal vein 1b in the organ 1 in the container 2 at the pipe 5 and the vein 1c of the organ 1 being prolonged externally of the container 2 via the exhaust pipe 7 capable of being connected to the vain 1c of the organ 1. Therefore, the temperature of the refrigerant 12 can be freely controlled by the mechanism B, the blood uniformly perfusing liquid, the refrigerating defect preventing agent and the low solidifying point final perfusing liquid can be suitably fed at the controlled temperature via the mechanism A to the organ 1, and yet the temperature of the container 2 can also be controlled by the mechanism C. Consequently, the perfusion of the organ 1 can be performed without undesired temperature gradient, and the method of preserving and thawing the organ can be performed without fail as described in detail above.

What is claimed is:

1. A method of preserving an organ comprising:

first perfusing step of injecting blood uniformly perfusing liquid such as choline from an artery or portal vein of the excised organ while gradually lowering its temperature and exhausting it from the vein, continuing said step until the liquid is lowered to the first proximity lowering temperature before its solidifying temperature, second perfusing step of perfusing refrigerating defect preventing agent such as dimethyl sulfoxide or glycerin instead of the blood uniformly perfusing liquid while gradually lowering its temperature from the first proximity lowering temperature, continuing said second step until the agent becomes the second proximity lowering temperature before its solidifying temperature, third perfusing step of perfusing the final perfusing liquid of low solidifying temperature lower than the agent such as alcohol or ether instead of the agent while gradually lowering the liquid from the second proximity lowering temperature, continuing said third step until the liquid becomes the third proximity lowering temperature before its solidifying temperature, or until the liquid is frozen, and preserving the frozen organ thus obtained in the frozen state.

2. A method of preserving an organ comprising:

first perfusing step of injecting blood uniformly perfusing liquid such as choline from an artery or portal vein of the excised organ while gradually lowering its temperature and exhausting it from the vein, continuing said step until the liquid is lowered to the first proximity lowering temperature before its solidifying temperature, second perfusing step of perfusing refrigerating defect preventing agent such as dimethyl sulfoxide or glycerin instead of the blood uniformly perfusing liquid while gradually lowering its temperature from the first proximity lowering temperature, continuing said second step until the agent becomes the second proximity lowering temperature before its solidifying temperature, third perfusing step of perfusing the final perfusing liquid of low solidifying temperature lower than the agent such as alcohol or ether instead of the agent while gradually lowering the liquid from the second proximity lowering temperature, continuing said third step until the liquid becomes the third proximity lowering temperature before its solidifying temperature, or until the liquid is frozen, preserving the frozen organ thus obtained in the frozen state, the first thawing and perfusing step of thawing the final perfusing liquid in the blood of said organ by gradually raising the organ thus preserved and frozen and then perfusing the liquid from said artery or portal vein to the vein while gradually raising the liquid, continuing said first thawing and perfusing step until becoming said second proximity lowering temperature, the second thawing and perfusing step of perfusing the agent instead of the liquid while gradually raising the temperature from said second proximity lowering temperature, continuing said second thawing the perfusing step until becoming said first proximity lowering temperature, the third thawing and perfusing step of perfusing the blood uniformly perfusing liquid instead of the agent while gradually raising the liquid from said first proximity lowering temperature, continuing said third thawing and perfusing step, and applying predetermined blood to said organ.

* * * * *